(12) United States Patent
Wazer et al.

(10) Patent No.: US 7,972,260 B2
(45) Date of Patent: Jul. 5, 2011

(54) RADIOACTIVE THERAPEUTIC APPARATUS (76) Inventors: David E. Wazer, Ashland, MA (US);
Thomas A. DiPetrillo, Dover, MA (US)

( * ) Notice: Subject to any disclaimer, the term of this patent is extended or adjusted under 35 U.S.C. 154(b) by 0 days.

(21) Appl. No.: 12/462,042

(22) Filed: Jul. 28, 2009

(65) Prior Publication Data

US 2009/0299125 A1 Dec. 3, 2009

(51) Int. Cl.
*A61N 5/00* (2006.01)
(52) U.S. Cl. ............................................................. 600/3
(58) Field of Classification Search ................ 600/1–8
See application file for complete search history.

(56) References Cited

U.S. PATENT DOCUMENTS

| | | | |
|---|---|---|---|
| 4,396,139 A * | 8/1983 | Hall et al. | 227/19 |
| 5,906,573 A | 5/1999 | Aretz | |
| 6,264,599 B1 | 7/2001 | Slater et al. | |
| 6,749,553 B2 * | 6/2004 | Brauckman et al. | 600/3 |
| 7,604,586 B2 * | 10/2009 | Wazer et al. | 600/3 |

OTHER PUBLICATIONS

Lee, Winnie et al., Limited Resection for Non-Small Cell Lung Cancer: Observed Local Control with Implantation of I-125 Brachytherapy Seeds, Ann Thorac Surg.; 2003; 75: pp. 237-243.
Voynov, George et al., "Intraoperative 125 I Vicryl Mesh Brachytherapy After Sublobar Resection for High-Risk Stage I Nonsmall Cell Lung Cancer," Brachytherapy 4 (2005) pp. 278-285.
Rodney J. Landreneau et al, "Wedge Resection Versus Lobectomy for Stage I (T1 NO MO) Non-Small-Cell Lung Cancer," The Journal of Thoracic and Cardiovascular Surgery, Apr. 1997, vol. 113, No. 4, pp. 691-698.
Ken Kodama, et al., "Intentional Limited Resection for Selected Patients with T1 NO MO Non-Small-Cell Lung Cancer: A Single-Institution Study," The Journal of Thoracic and Cardiovascular Surgery, Sep. 1997, vol. 114, No. 3, pp. 347-353.
Erik H. Fleischman et al., "Iodine125 Interstitial Brachytherapy in the Treatment of Carcinoma of the Lung," Wiley InterScience: Journal: Abstract, Journal of Surgical Oncology, vol. 49, Issue 1, pp. 25-28, published online: Jul. 20, 2006.
Dattatreyudu Nori et al., "Intraoperative Brachytherapy Using Gelfoam Radioactive Plaque Implants for Resected State III Non-Small Cell Lung Cancer with Positive Margin: A Pilot Study," Journal of Surgical Oncology, vol. 60, Issue 4, pp. 257-261, 1995.
Thomas J. Birdas et al., "Sublobar Resection with Brachytherapy Versus Lobectomy for Stage Ib Nonsmall Cell Lung Cancer," Ann Thorac Surg, 2006; 81 pp. 434-439.
Baxil S. Hilaris et al., "The Role of External Radiation and Brachytherapy in Unresectable Non-Small Cell Lung Cancer," Surgical Clinics of North America, vol. 67, No. 5, Oct. 1987, pp. 1061-1071.
Ravinder Nath et al., "Dosimetry of Interstitial Brachytherapy Sources: Recommendations of the AAPM Radiation Therapy Committee Task Group No. 43," Medical Physics, vol. 22, No. 2, Feb. 1995, pp. 209-234.

(Continued)

*Primary Examiner* — John P Lacyk
(74) *Attorney, Agent, or Firm* — David M. Driscoll, Esq.

(57) ABSTRACT

A method and device for applying a radioactive source to a tissue site is disclosed. The device facilitates the precise placement of, for example, $^{125}$Iodine seeds relative to the surgical margin, assures the seeds remain fixed in their precise position for the duration of the treatment, overcomes the technical difficulties of manipulating the seeds through the narrow surgical incision, and reduces the radiation dose to the clinicians. The device incorporates the radioactive seeds into a fastening means, preferably surgical staples, used in the surgical procedure. In this way, the seeds are concurrently secured in position directly adjacent to the surgical resection and remain immobile.

13 Claims, 10 Drawing Sheets

OTHER PUBLICATIONS

Julianna Pisch et al., "Placement of 125I Implants with the Da Vinci Robotic System After Video-Assisted Thoracoscopic Wedge Resection: A Feasibility Study," Int. J. Radiation Oncology Biol. Phys., vol. 60, No. 3, pp. 928-932, 2004.

Alex Chen et al., "Intraoperative 125I Brachytherapy for High-Risk Stage I Non-Small Cell Lung Carcinoma," Int. J. Radiation Oncology Biol. Phys., vol. 44, No. 5, pp. 1057-1063, 1999.

Robert T. Heelan et al., "Lung Tumors: Percutaneous Implantation of I-125 Sources with CT Treatment Planning 1," Radiology, Sep. 1987, pp. 735-740.

Robert J. Ginsberg et al., "Randomized Trial of Lobectomy Versus Limited Resection for T1 N0 Non-Small Cell Lung Cancer," Ann. Thorac. Surg., 1995, vol. 60, pp. 615-623.

* cited by examiner

RADIOACTIVE THERAPEUTIC APPARATUS

RELATED APPLICATION

Priority for this application is hereby claimed under 35 U.S.C. §119(e) to commonly owned and co-pending U.S. Provisional Patent Application No. 60/792,733 which was filed on Apr. 18, 2006. The content of all of the aforementioned application is hereby incorporated by reference herein in its entirety.

TECHNICAL FIELD

The present invention relates to an improved method and system for applying a radioactive source to a tissue site. More particularly, the present invention pertains to an improved delivery system based upon the incorporation of a radioactive seed by fastening means, such as a surgical staple. More specifically, the present invention pertains to an improved brachytherapy delivery system for applying a radioactive source to a tissue site.

BACKGROUND DISCUSSION

The incidence of lung cancer has been rising over the last half century, although the rate has decreased somewhat over the last decade. The American Cancer Society estimates the number of new cases in 2006 to exceed 174,000. Lung cancer is the leading cause of cancer deaths in the United States among both men and women, claiming more lives than colon, prostate and breast cancer combined.

Non-small cell lung cancer (NSCLC) is the most commonly diagnosed form of the disease, affecting 4 out of 5 patients. In North America, 75% of patients are present with the early-stage (T1, T2) disease. In most cases, early stage NSCLC can be treated successfully with surgery if the cancer has not spread beyond the chest. Surgical resection is the definitive treatment and lobectomy is the procedure of choice. Lobectomy is the most common type of lung cancer surgery, involving removal of an entire lobe of one lung. For these early stage NSCLC patients, lobectomy yields a 5-year survival rate of 65-77%. Locoregional recurrence occurs in 28% of T1N0 tumors submitted to thoracotomy, with the highest initial failure rates detected in the ipsilateral hemithorax. Unfortunately, some patients with this disease are poor candidates for lobectomy due to poor pulmonary health or other medical issues.

Stage I NSCLC patients with compromised cardiopulmonary status may undergo limited surgical resections in an attempt at lung preservation while achieving adequate resection margins. However, lesser resections have been associated with an increased risk of local recurrence, even for small peripheral tumors.[i] Nonetheless, limited resection is viewed as an acceptable alternative for patients with poor physiologic reserve or of advanced age.

Though sublobar resection alone is associated with an increased incidence of post-operative disease recurrence, it is still advocated for high risk patients in the absence of a good alternative. External beam radiation therapy has been used successfully to reduce the risk of local recurrence in these compromised patients. However, external beam radiation therapy further reduces pulmonary function because it generally requires the beam to pass through normal lung to reach the target lesion. Some studies suggest that adding brachytherapy to the regimen can make a dramatic difference in outcomes.

Brachytherapy has a long history of use in the treatment of lung cancer patients. Prior studies have shown improved local control using Iodine permanent implants as a radiation boost for Stage III NSCLC with paraspinal or chest wall involvement. Intraoperative brachytherapy has been shown to be an effective therapeutic modality for patients unable to undergo a surgical lobectomy; it is an alternative to external beam irradiation for patients who cannot tolerate further loss of lung function.

D'Amato et al. at Allegheny General Hospital reported favorable results using a brachytherapy technique to implant $^{125}$Iodine seeds for improving local control in patients undergoing thoracoscopic wedge resection for peripheral stage I lung cancer. A series of fourteen patients with non-small cell cancer and significant impairment in cardiopulmonary function having small peripheral solitary pulmonary nodules underwent video-assisted thoracoscopic wedge resection and intraoperative $^{125}$Iodine seed brachytherapy. At a mean follow-up of 7 months (range, 2 to 12 months), there were no cases of significant radiation pneumonitis or local recurrence. They concluded intraoperative brachytherapy appears to be a safe and efficient alternative to external-beam radiation therapy when adjuvant radiotherapy is considered following therapeutic wedge resection of stage I (T1N0) lung cancers.

Lee et al. at Tufts New England Medical Center reported the results of limited resection for non-small cell lung cancer and the observed local control achieved with the implantation of $^{125}$Iodine brachytherapy seeds. Their series consisted of 35 patients who were deemed not to be candidates for a lobectomy or pneumonectomy due to compromised pulmonary function or cardiac indication. These candidates underwent wedge resection (32 patients), segmental resection (2 patients) and lobectomy (1 patient). All patients received $^{125}$Iodine seed placement along the resection margin to deliver a dose of 125 to 140 Gy at a 1-cm depth. Their results suggest that limited resection is a reasonable alternative to nonoperative management of lung cancers for compromised patients, particularly those with stage IA lung cancers. The implantation of $^{125}$Iodine brachytherapy seeds is effective in reducing the recurrence at the resected lung margin.

Birdas et al. reported further on the work of the Allegheny General Hospital group. They had previously shown that intraoperative brachytherapy decreased the local recurrences associated with sublobar resections for small stage IA NSCLC. In this report, they presented the outcomes of sublobar resection with brachytherapy compared with lobectomy in patients with stage Ib tumors. They retrospectively reviewed 167 stage IB NSCLC patients: 126 underwent lobectomy and 41 sublobar resection with $^{125}$Iodine brachytherapy over the resection staple line. Endpoints were perioperative outcomes, incidence of recurrence, and disease-free and overall survival. Patients undergoing sublobar resections had significantly worse preoperative pulmonary function. Hospital mortality, nonfatal complications, and median length of stay were similar in the two groups. Median follow-up was 25.1 months. Local recurrence in sublobar resection patients was 2 of 41 (4.8%), similar to the lobectomy group: 4 of 126 (3.2%; p=0.6). At 4 years, both groups had equivalent disease-free survival (sublobar group, 43.0%; median, 37.7 months; and lobectomy group, 42.8%; median 41.8 months, p=0.57) and overall survival (sublobar group, 54.1%; median, 50.2 months; and lobectomy group, 51.8%; median, 56.9 months; p=0.38). They concluded that sublobar resection with brachytherapy reduced local recurrence rates to the equivalent of lobectomy in patients with stage Ib NSCLC, and resulted in similar perioperative outcomes and disease-free and overall survival, despite being used in patients with compromised lung function. They recommend the addition of intraoperative brachytherapy to sublobar resections in stage Ib patients who cannot tolerate a lobectomy.

These early indications of the efficacy of brachytherapy used in conjunction with sublobular resection for compromised patients have set the stage for a planned national, multi-center clinical trial by the American College of Surgeons Oncology Group and NTH. This Phase III trial, identified as NCT00107172, is currently enrolling patients. These studies and the Phase III clinical trial clearly demonstrate the potential for intraoperative brachytherapy for those non-small cell lung cancer (NSCLC) patients with compromised cardiopulmonary status who are not candidates for lobectomy.

One main problem facing this technique is in the ability to precisely deliver the brachytherapy seeds intraoperatively to achieve the proper dose distribution and minimize the radiation dose to the clinicians performing the procedure.

Under one practice, Pisch et al. have reported on a technique in which loose seeds were manually delivered via a Mick® applicator. Although they did not describe the surgical procedure, they did state that they made multiple passes in the king parenchyma. Consequently, this procedure would not have been possible through a thoracoscopy port, which would be a potential problem in patients with chronic obstructive pulmonary disease. They also did not discuss seed migration, which would be expected to be a significant issue.

Figure 1:
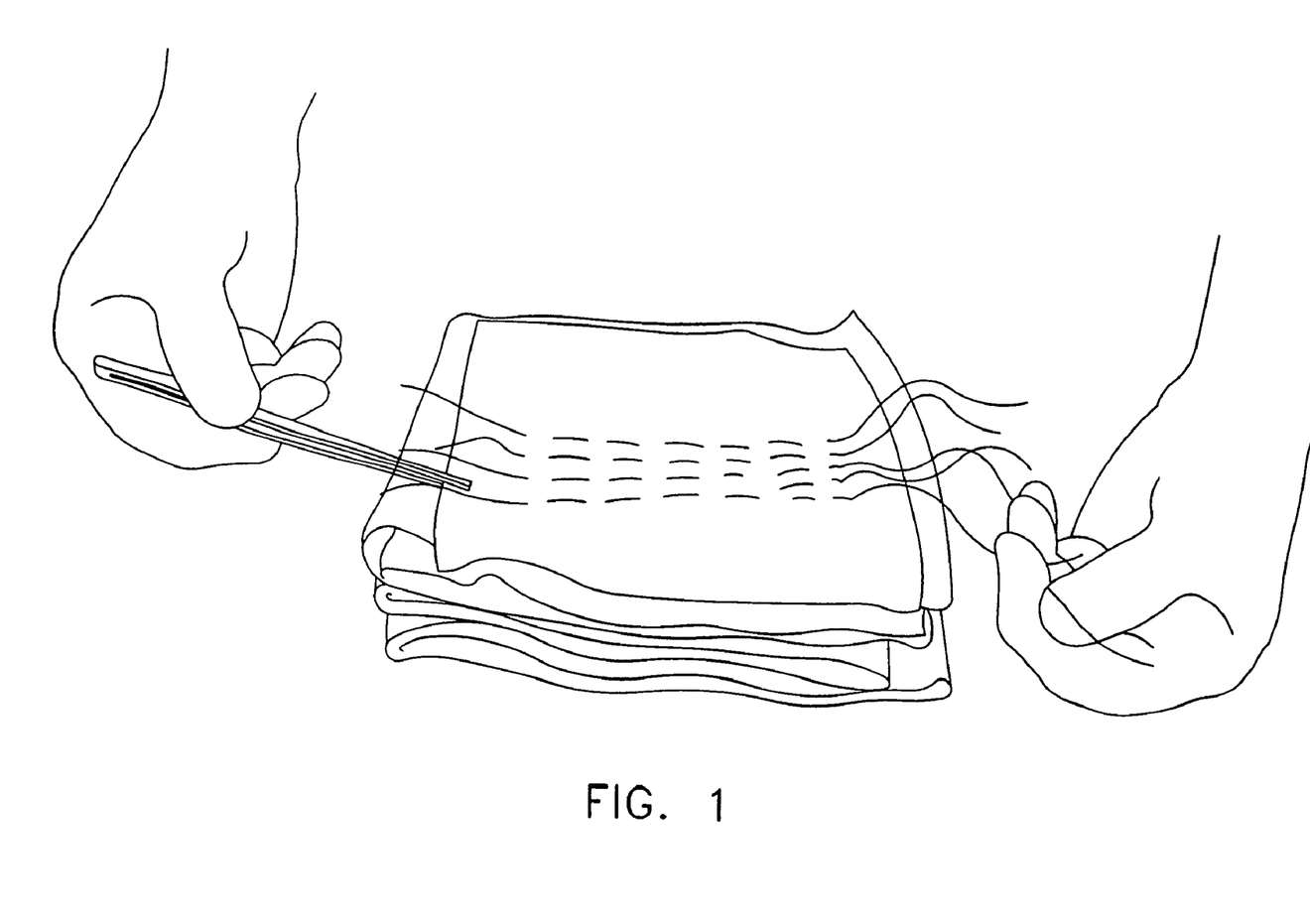
FIG. 1 is a schematic diagram of the insertion of radioactive seeds through a thoracoscopy port with video assistance.

Chen et al. developed an intraoperative technique utilizing vicryl mesh imbedded with $^{125}$Iodine radioactive seeds for thoracoscopic placement over the tumor bed and staple line after video-assisted thoracoscopic resection. $^{125}$Iodine seeds, spaced 1 cm apart, were embedded into a hollow vicryl suture material. These seeds were attached to a sheet of appropriately sized vicryl mesh with sutures and/or surgical clips at each end. The spacing between rows was adjusted to deliver a dose of 100-120 Gy at 0.5 cm. Radiation protection was achieved during this preparatory step by the use of a custom leaded-plexiglas, autoclavable shield within which the mesh was assembled. The $^{125}$Iodine vicryl mesh was then inserted through the thoracoscopy port and sutured over the tumor bed and resection line. As the radioactive mesh was implanted with video assistance over a relatively flat resection surface, it would lay over the surgical bed without any source overlap. Postoperative, orthogonal simulation films were obtained for placement verification and computer dosimetry. Although this procedure solves the problem of seed migration, it presents other difficulties. As shown in the photographs of the paper, delivery of the mesh through the thoracoscopy port is a difficult procedure and one with appreciable dose to the physician. Proper positioning of the mesh in relation to the surgical margin is critical and difficult. Because the seeds are secured in the mesh prior to insertion, they rely on the proper positioning of the mesh in relation to the target to achieve the desired dose distribution. FIG. 1 illustrates this mesh/seed arrangement.

Lee et al. have reported on a technique that solves some of these problems. In this technique, patients undergoing wedge resection have an incision as small as possible, sometimes as small as 5 cm in length. The resection is earned out using either a linear gastrointestinal stapler or an endostapler. They intend to achieve a minimum gross margin >1 cm around the tumor.

Figure 2:
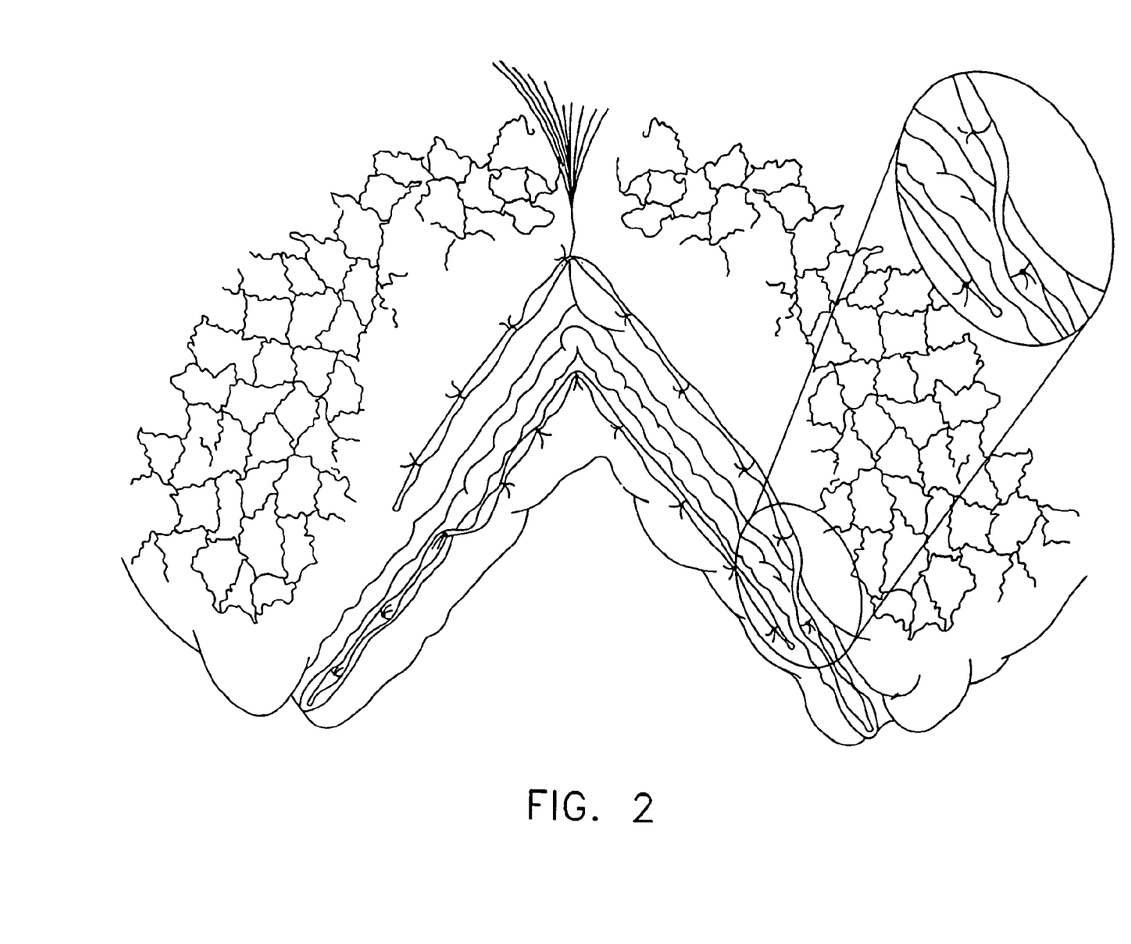
FIG. 2 is a representation of a portion of the human lung in which a wedge resection has been performed.

Strands often $^{125}$Iodine brachytherapy seeds, embedded in polyglactin 910 suture with 1 cm spacing were affixed along the resection margin or 0.5 cm on either side of the margin, depending upon the source strength, length of the resection margin, and the number of seeds available. In most cases, from one to three strands were affixed on both sides of the resection margin over its entire length, utilizing interrupted sutures of 3-0 silk spaced approximately 2 cm apart. Whenever an insufficient number of seeds were available to cover the entire resection margin with parallel strands, the most peripheral portion of the resection margin was affixed with a single strand, and the more central portion affixed with parallel strands on either side of the stapled margin. FIG. 2 shows an example of this technique. Source strength was chosen to deliver a combined radiation dose of 125-140 Gy at a depth of 1 cm. FIG. 2 shows a portion of lung in which a wedge resection has previously been carried out. Each limb of the wedge resection is approximately 6 cm in length. Shown is how two multi-seed strands would be affixed to the margin. The most peripheral seeds are placed directly in the margin, and the deeper portions of the wedge have two strands of seeds affixed to the lung spaced approximately 1 cm apart or 0.5 cm from the resection margin. Simple 3-0 silk sutures may be used to hold the strands in place.

This technique has a better possibility of positioning the seeds at the appropriate position relative to the resection margin. However, the radiation dose to the hands of the radiation oncologist/surgeon is significant. Even through the use of relatively thin lead gloves, the reduction in dose is limited. The use of thicker, more heavily shielded lead gloves limits the dexterity sufficiently as to be impractical.

To address this problem, Pisch et al. have reported on an evaluation of the feasibility of using the da Vinci robotic system (Intuitive Surgical) for radioactive seed placement in the wedge resection margin. Their study was of pigs' lungs. Video-assisted thoracoscopic wedge resection was performed in the upper and lower lobes in pigs. Dummy $^{125}$Iodine seeds embedded in absorbable sutures were sewn into the resection margin with the aid of the da Vinci robotic system, without complications. In the "loop technique," the seeds were placed in a cylindrical pattern; in the "longitudinal," they were above and lateral to the resection margin. Orthogonal radiographs were taken in the operating room. Calculated doses at 1 cm ranged from 70 Gy to 107 Gy depending upon the technique. They concluded that robotic technology allows direct placement of radioactive seeds into the resection margin by endoscopic surgery. It overcomes the technical difficulties of manipulating in the narrow chest cavity. With the advent of robotic technology, new options in the treatment of lung cancer, as well as other malignant tumors, will become available. However, this is a complicated and expensive solution.

Other prior art is shown in U.S. Pat. No. 5,906,573 to Aretz and U.S. Pat. No. 6,264,599 to Slater et al. The Aretz '573 patent describes a radioactive surgical fastening device in which a radioisotope is incorporated by ion implantation. The Slater et al '599 patent describes radioactive therapeutic seeds which have means for engaging the tissue surrounding the seeds when the seeds are implanted. Although these patents disclose the concept of associating a radioactive source with a fastener, none of these prior art references teach incorporating a radioisotope into a fastener that is used in the actual surgical procedure, particularly as part of a surgical staple, ha, for example, the Slater et al '599 patent they describe the use of an engagement means for positioning therapeutic seeds, however, their engagement means is positioned independent of any surgical operation and is not intended for use as a means for conducting any part of a surgical procedure.

Accordingly, it is an object of the present invention to provide an apparatus or device for incorporating a radioactive source into or with a surgical procedure means such as a surgical staple so that the radioactive source can be positioned concurrently with the application of the surgical tissue securing means.

BRIEF SUMMARY OF THE INVENTION

The present invention facilitates the precise placement of, for example, $^{125}$Iodine seeds relative to the surgical margin, assures the seeds remain fixed in their precise position for the duration of the treatment, overcomes the technical difficulties of manipulating the seeds through the narrow surgical incision, and reduces the radiation dose to the clinicians. The concepts of the present invention incorporate the radioactive $^{125}$Iodine seeds into a fastening means, preferably surgical staples, used in the surgical procedure. In this way, the seeds are concurrently secured in position directly adjacent to the surgical resection and remain immobile. They are precisely located relative to the resection, placed by a very convenient method eliminating the difficulties of working through the narrow surgical incision. The seed position is rigidly fixed, assuring that the dose distribution does not uncontrollably change over the duration of the treatment. This method permits the dose distribution to be precisely planned prior to the surgery to achieve the desired result. Insertion of the seeds in conjunction with the application of the staples also significantly reduces the dose to the clinician. The seeds/staple are incorporated into the staple cartridge to provide shielding during insertion.

In one embodiment there is provided an apparatus for implanting a radioactive source into human tissue, comprising: a fastening means including at least one staple having a base and tissue piercing ends; a sleeve for receiving said radioactive source; and means for securing said sleeve to said fastening means. The staple is positionable for piercing the tissue in performing a surgical procedure while concurrently securing the radioactive source in a fixed position and at a position that is adjacent to the site where the surgical procedure has been performed.

In accordance with other aspects of the present invention the apparatus may be used for a brachytherapy delivery system for applying a radioactive source to a tissue site at a resection margin; the sleeve may be constructed of any one of platinum, titanium, nickel-titanium alloys, gold, stainless steel, palladium, silica and alumina; the sleeve may comprise a tube having legs extending therefrom to form the legs of the staple; the sleeve may be secured to the staple by means of laser welding; and there may be provided a pair of staples that are arranged to be secured by a common sleeve that extends therebetween.

In accordance with another embodiment of the invention there is provided a device for positioning a radioactive source into human tissue, comprising: a fastening means including an array of staples each having a base and tissue piercing ends with the base formed as a tubular cavity for receiving and holding the radioactive source therein. The tissue piercing ends form legs of the staple. The staple is positionable for piercing the tissue in performing a surgical procedure at a surgical margin while concurrently securing the radioactive source in a fixed position at the surgical margin.

In accordance with another embodiment of the present invention there is provided a method for positioning a radioactive source at a surgical margin between human tissue for therapeutic purposes, comprising the steps of, providing a series of staples that are adapted for use in a surgical procedure to join tissue at the surgical margin, integrally forming a radioactive source associated with each staple, and applying the staples in sequence at the surgical margin while concurrently securing the radioactive source in a fixed position at or adjacent to the surgical margin.

DESCRIPTION OF THE DRAWINGS

Numerous other objects, features and advantages of the present invention are now realized by a reading of the following detailed description taken in conjunction with the accompanying drawings, in which.

DETAILED DESCRIPTION

An objective of the present invention is to develop an improved delivery system based upon the incorporation of a radioactive seed into fastening means, preferably into a surgical staple. More particularly the disclosed system is an improved brachytherapy delivery system for treatment of, inter alia, lung cancer based upon the incorporation of radioactive $^{125}$Iodine seeds into surgical staples used in lung resection. For patients with compromised cardiopulmonary status, the inclusion of brachytherapy with sublobular resection has shown a significant improvement in therapeutic outcome over sublobular resection alone. This present technique facilitates the delivery of this therapy. Furthermore, the techniques described herein may also be used in other medical procedures. Moreover, the techniques of the present invention may be used in applying other radioactive sources than the specific ones disclosed herein.

Brachytherapy has the obvious advantage of maximally irradiating the tumor bed while sparing surrounding normal tissue from the field of radiation. This approach has been especially useful when the required radiation dose exceeds the tolerance dose of the surrounding normal tissues. However, logistic issues have limited the application of brachytherapy particularly in lung cancer applications.

An objective of the present invention is to develop a simplified method for radioactive sources, particularly $^{125}$Iodine sources, in conjunction with the surgical staples used during the resection procedure to permit the application of brachytherapy at the same time as the surgery is being performed. The technique of the present invention facilitates the precise placement of, for example, $^{125}$Iodine seeds relative to the surgical margin, assures the seeds remain fixed in their precise position for the duration of the treatment, overcomes the technical difficulties of manipulating the seeds through the narrow surgical incision, and reduces the radiation dose to the clinicians.

This development extends the use of brachytherapy to a much larger number of compromised lung cancer patients for whom more traditional surgical procedures, such as lobectomy, are not an option. Several studies have shown the use of radioactive brachytherapy to have a clinical benefit for compromised lung cancer patients for whom more traditional surgical procedures, such as lobectomy, are not an option.

A preferred embodiment of the present invention demonstrates a more feasible method for the intraoperative delivery of the $^{125}$Iodine sources in both safety and effectiveness for treatment of lung cancer.

The demonstration of treatment efficacy combined with this improvement in seed delivery encourages the use of this technique for NSCLC patients with compromised cardiopulmonary status who are not candidates for lobectomy. This development affords the additional clinical benefit of brachytherapy to these patients, thereby improving their outcomes. The improved dose distribution resulting from more precise source positioning and fixation is expected to improve the currently identified clinical benefit of brachytherapy due to the limitations of current techniques. Because lung cancer is the leading cause of cancer deaths in the United States, any improvement in clinical outcome resulting from this program translates into significant societal benefit.

These large numbers of prospective patients for this technique also make this project commercially viable. It is further anticipated that a demonstration of treatment efficacy for lung cancer encourages the use of this radionuclide for brachytherapy of other soft-tissue/small-organ carcinomas where conformal dose distribution around the surgical resection margin and operator safety are critical. This development for the improved delivery of $^{125}$Iodine brachytherapy sources has additional applications in brachytherapy. The use of low energy/high activity radiation sources has widespread applications in brachytherapy.

The present invention develops a brachytherapy system that can be used for intraoperative placement of radioactive seeds simultaneously with fastener means, preferably surgical staples, used in lung wedge resection procedures. Such a device precisely fixes the position of the seeds relative to the resection margin and provide a well defined, stable dose distribution to the target, while facilitating the means for delivering these seeds with reduced dose to the physicians. In one embodiment this is performed by having the radiation source integral with the fastener or staple so that when the resection occurs, concurrently therewith, the radiation source is properly positioned.

Figure 3:
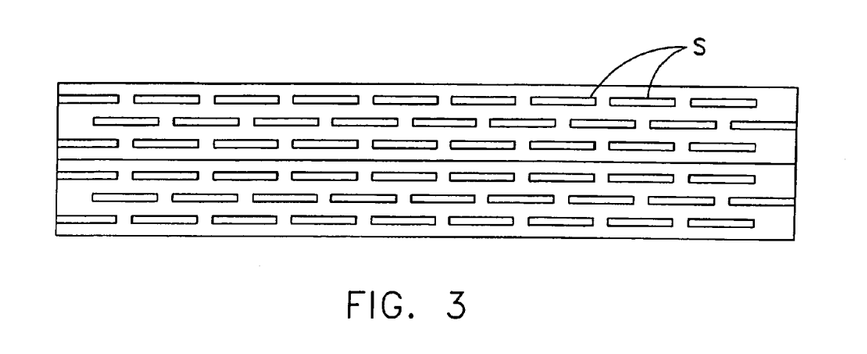
FIG. 3 is an example of the staple pattern in a typical surgical stapling system.

The technology of surgical staples and their delivery system is mature. Elements such as wire thickness/diameter, staple length and spacing have all been designed and validated for their specific purpose. Any modification to accommodate radioactive $^{125}$Iodine seeds should avoid any compromise of these parameters. The design should incorporate currently used surgical staples, which are fabricated from wires ranging from 0.21 to 0.28 mm diameter, with, widths ranging from 3 to 4 mm and leg-lengths ranging from 2.5 to 4.8 mm. These staples are typically spaced ~1.0 mm apart both longitudinally and laterally, such as shown by the staples S in the pattern of FIG. 3. The design should permit delivery of the seeds and surgical staples using currently-available surgical stapling instruments. The seed/staple combination should be easily assembled into the staple cartridge. The combination should be readily sterilizable. The combination should be deliverable with minimal radiation exposure to the physician. The design of any additional structure around the $^{125}$Iodine seed should be sensitive to excessive modulation of the dosimetric parameters of the seed. Refer to FIG. 3 that illustrates an example of the staple pattern in a surgical stapling system.

Figure 4:
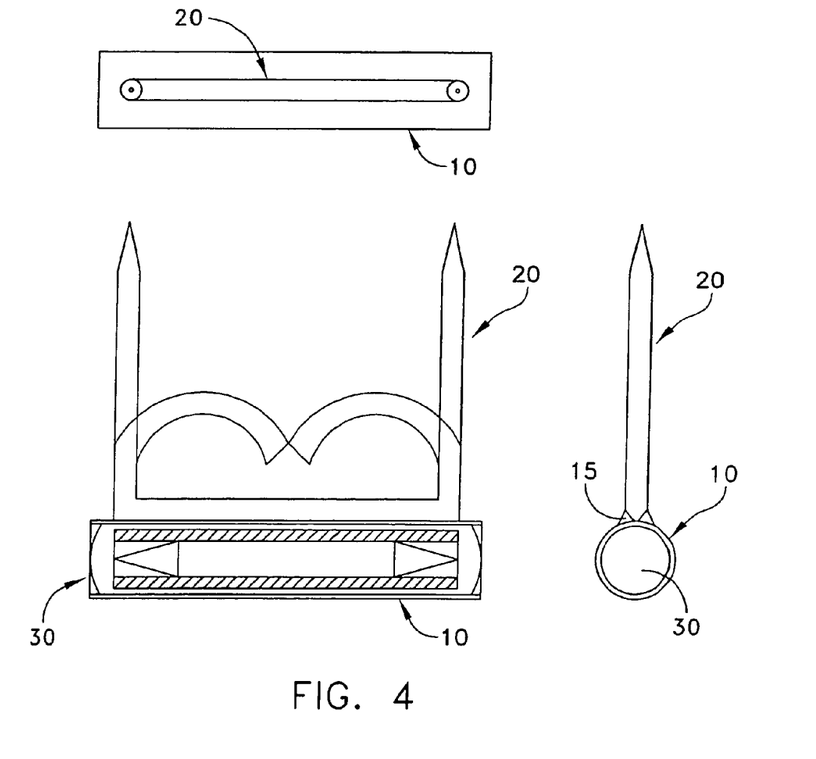
FIG. 4 is an illustration of a single staple that is attached with a retaining sleeve that accommodates a radioactive seed and as in accordance with the present invention.

One embodiment in accordance with the present invention is shown in FIG. 4 and includes the attachment of a sleeve 10 to a single surgical staple 20 by means of laser welding at 15. The sleeve 10 may be of 0.9 mm OD×0.8 mm ID and accommodates a standard radioactive $^{125}$Iodine seed 30, as illustrated in FIG. 4. A standard seed is 4.5 mm long, which is longer than an individual staple. This could be accommodated in the cartridge in such a way as to not interfere with adjacent staples. The radioactive $^{125}$Iodine seed 30 is inserted and fixed within the sleeve 10. As noted in FIG. 4, the radioactive source and sleeve are preferably symmetrically located relative to the staple 20. FIG. 4 also shows, the staple in both a rest position and a released bent position. It is noted that the legs of the staple are pointed as usual.

Figure 5:
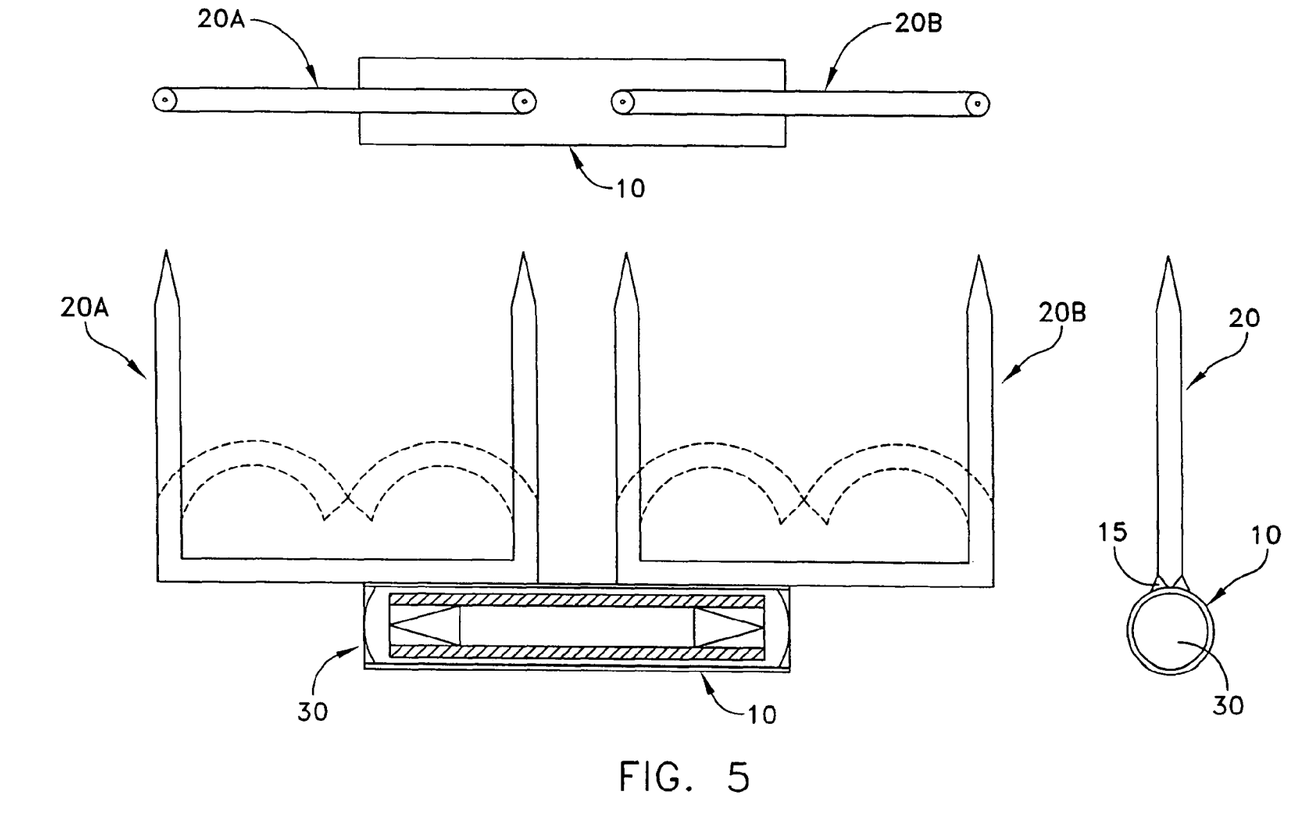
FIG. 5 is a further example, like that shown in FIG. 4, but using a pair of staples interconnected with a single, sleeve.

An alternative embodiment, as shown in FIG. 5, illustrates the attachment of a sleeve 10 to two adjacent staples 20A and 20B, thereby accommodating the length and providing an additional measure of stability. As noted in FIG. 5, the sleeve is preferably symmetrically located relative to the pair of staples 20. The sleeve 10 bridges between the adjacently disposed staple pair, secured by means of the laser weld. The sleeve preferably is in contact with each staple over a like length so as to provide the symmetry. FIG. 5 also shows the staples in both a rest position and a released bent position.

Other securing means may also be provided to attach the sleeve to the staple. For example, an adhesive could be used, as long as the attachment location is secure and does not disengage during use. Thus, the system of the present invention provides an integral fastener in which the radiation source is integrally formed with the fastener, and usable in a surgical procedure.

Clearly, the addition of structure around the $^{125}$Iodine seed modulates the dose distribution around the seed. In order to account for this, a study of the dose distribution around the seed/staple combination is simulated using Monte Carlo techniques.

A full theoretical radiation-dose profile is computed using Monte Carlo techniques for a single $^{125}$Iodine Seed/Staple Combination to estimate radiation dosimetry at clinical points of interest. The modeled configuration includes the structural configuration of the sleeve and staple, as well as the detailed composition of the $^{125}$Iodine seed itself. Although the dosimetric parameters of all currently-available $^{125}$Iodine seed have been measured and reported, these parameters will be different by the modulation provided by the sleeve and staple. It is desired to characterize this specific design to properly plan a treatment.

One element of particular note is that typical brachytherapy seeds and high dose rate sources are axially symmetric. The standard formalism for describing the dosimetric aspects of these seeds/sources, the Report of AAPM Task Group 43, is based on the assumption of axial symmetry. In this case, due to the location of the staple on one side of the seed, the dose distribution is expected to be axially asymmetric. Consequently, the formalism of AAPM TG-43 is not directly applied, but rather characterized in a 3-D representation.

The Monte Carlo calculation is performed using the MCNP Version 5 Monte Carlo computer code, developed by LANL. The MCNP5 Monte Carlo code is a general neutron, photon, and electron radiation transport code that facilitates modeling complicated three-dimensional, heterogeneous geometrical structures such as medical sources and applicators. The simulation geometry mimics the geometrical and elemental compositions of the source and its surrounding structure. The spatial resolution of the computed dose distribution can be as small as 100 μm. Its photon transport model includes photoelectric effect and accompanying fluorescence emission, coherent (Thomson) scattering, Compton scattering and pair production. A continuous-slowing-down model is used for electron transport that includes positrons, K x-rays and bremsstrahlung. MCNP is the only widely-used radiation transport code that permits coupled transport of photons, electrons, and neutrons.

The dose distribution is calculated for radial distances ranging from 0.5 to 10 cm over polar angles ranging from 0° to 180° and azimuthal angles from 0° to 360°. The calculated dose distribution is deconvolved into a 3-D dose kernel for use with our treatment planning system that conforms as closely as practical with the formalism described by AAPM TG-43. This characterizes the dose rate constant, Λ, the radial dose function, $g_L(r)$, and the geometry function, $G_L(r,\theta)$. However, this characterizes a 3-D anisotropy function, $F(r,\theta,\square)$, rather than the 2-D anisotropy function, $F(r,\theta)$, recommended by TG-43.

The dose distribution in the surgical resection target is evaluated for clinical suitability. Studies have specified that the dose delivered to up to 1 cm from the resection margin should be 125-140 Gy. A treatment with seed positions is selected to achieve that goal.

Figure 6:
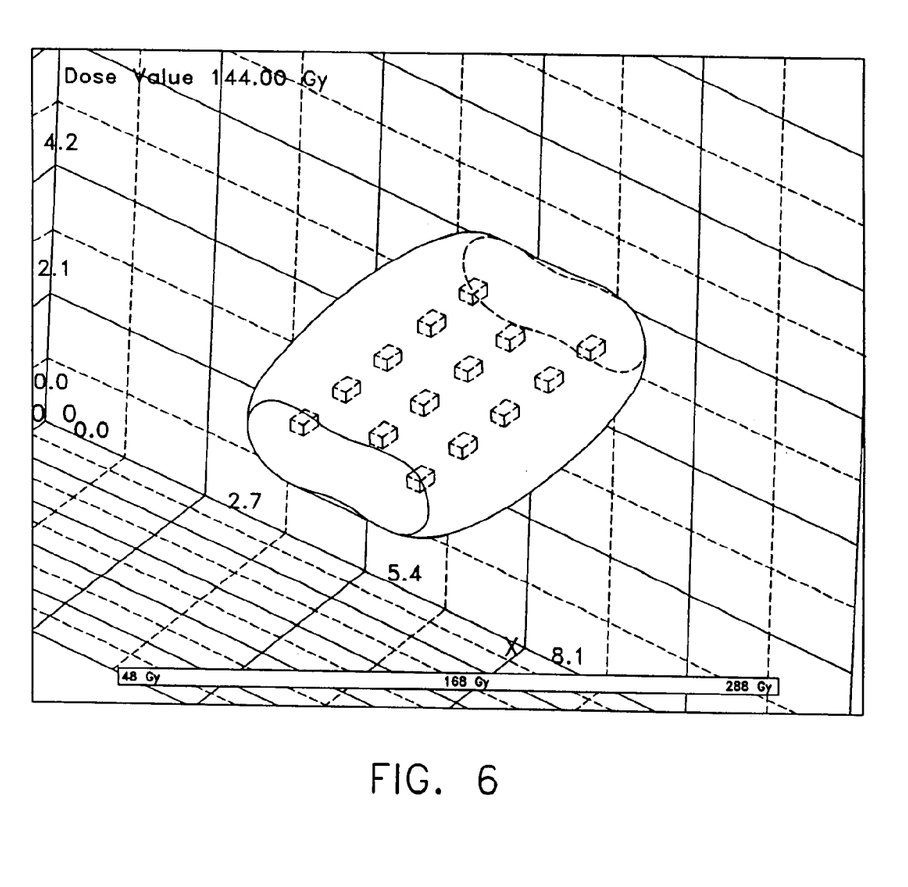
FIG. 6 illustrates a plan for a single resection margin with an axially symmetric seed.

In most brachytherapy situations, this treatment plan could be performed using a standard treatment planning system. FIG. 6 shows a typical plan for a single resection margin using a standard treatment planning system with axially symmetric seed dosimetry. However, the I-Plant TPS, as well as all other commercial treatment planning software assume axially symmetric dose distributions in their calculational algorithms. Consequently, standard treatment planning software does not account for axial asymmetry and therefore does not provide precise results. We will develop a modification to our existing Treatment Planning Software to accommodate the three-dimensional dosimetry kernel for this application. Using this new module, a series of treatment plans are performed to achieve the dose specification. The design objective of the treatment is to deliver a dose of 125-140 Gy to the target region within 1 cm of the surgical resection margin. This creates an optimized treatment plan to meet this objective. The adapted treatment planning system is used to optimize the number and position of seeds within the constraints of the available positions within the cartridge.

These treatment plans are dosimetrically evaluated. The treatment planning system calculates the implant dose distribution for each geometry. A dose-volume histogram (DVH) is constructed from the dose distribution, and analyzed with respect to the defined volumes. From the DVH, we determine the volume and percent of target volume receiving 100% of the prescription dose ($V_{100}$), receiving 150% of the prescription dose ($V_{150}$), and receiving 200% of the prescription dose ($V_{200}$). We also compute the minimum dose received by more than 90% of the target volume ($D_{90}$) and its relationship to the prescription volume.

Dosimetric quality of the implant is evaluated using criteria including the mean central dose (MCD), average peripheral dose (APD), and percentage deviation between the APD and the prescription dose (DAV). Implants are also evaluated using the dose homogeneity index (DHI), defined as:

$$DHI = \frac{V_{100} - V_{150}}{V_{100}}$$

The successful treatment plan has MCD, APD and $D_{90}$ values closest to the prescription dose of 125-140 Gy, the highest DHI, and the lowest $V_{200}$.

From the design criteria being observed for the $^{125}$Iodine seed/staple combination, it is intended to make as few modifications to the staple cartridge as are necessary. One criterion that would be inviolate is the positioning of the staples. Within this constraint, we would make the modifications necessary to the design of the cartridge insert to accommodate the additional space needed for the seed/sleeve combination. As the number of seeds required are far lower than the number of staples used, we expect the introduction of seeds will have minimal impact.

The cartridges for the surgical staples may be molded in plastic. This material does not provide any appreciable shielding, even for such a low energy radionuclide as $^{125}$Iodine. However, high density plastics containing tungsten are available and are regularly used for radiation shielding for $^{125}$Iodine seeds. We would plan to fabricate the special cartridge using this type of plastic. The cartridge would be designed to provide adequate shielding for the clinicians handling this device during the surgical procedure.

Figure 7:
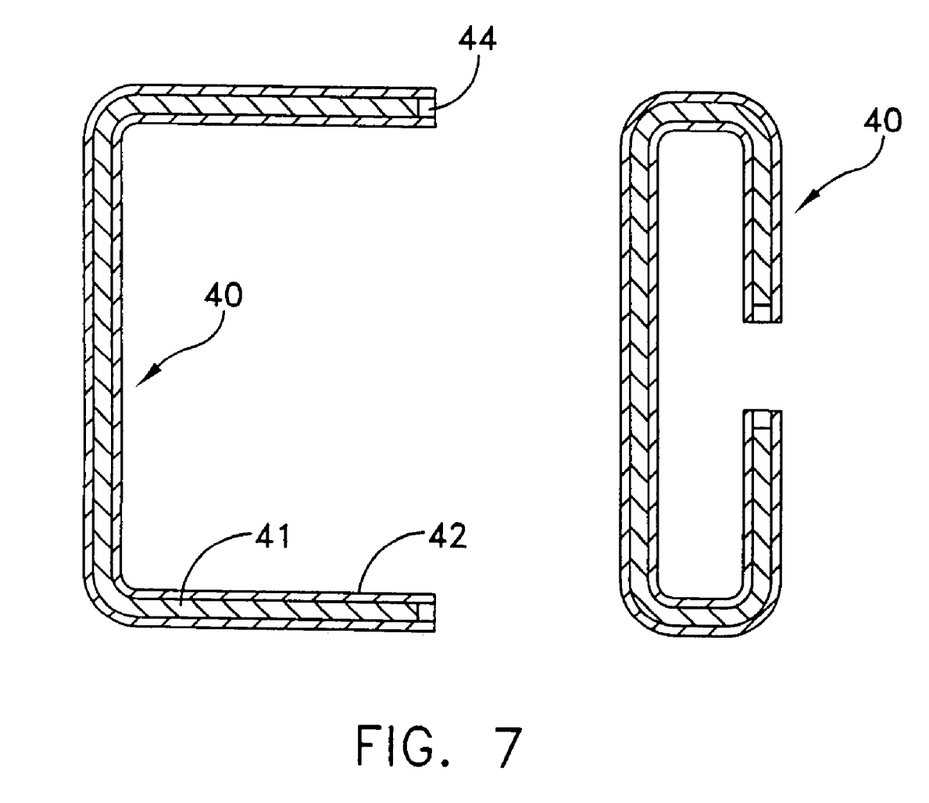
FIG. 7 illustrates another staple configuration in accordance with the present invention.

Another embodiment in accordance with the present invention is shown in FIG. 7 and includes an integrally formed staple structure shown in both open and closed positions. This is comprised of a radioactive center element 41 and an encapsulating outer element 42. The ends 44 are shown blunt but in practice would be pointed so as to function as a surgical staple. The base of the staple is preferably about 3 inches and each leg, in the open position is about 2 inches. These can be readily accommodated in a conventional staple delivery cartridge.

As mentioned previously currently-used surgical staples are fabricated from titanium wires ranging from 0.21 to 0.28 mm diameter, with widths ranging from 3 to 4 mm and leg-lengths ranging from 2.5 to 4.8 mm. These staples are typically spaced ~1.0 mm apart both longitudinally and laterally, as shown in the pattern of FIG. 3. However, the surgical stapling instruments used to deliver these staples can accommodate staples with diameters even as large as 0.50 mm.

Figure 8:
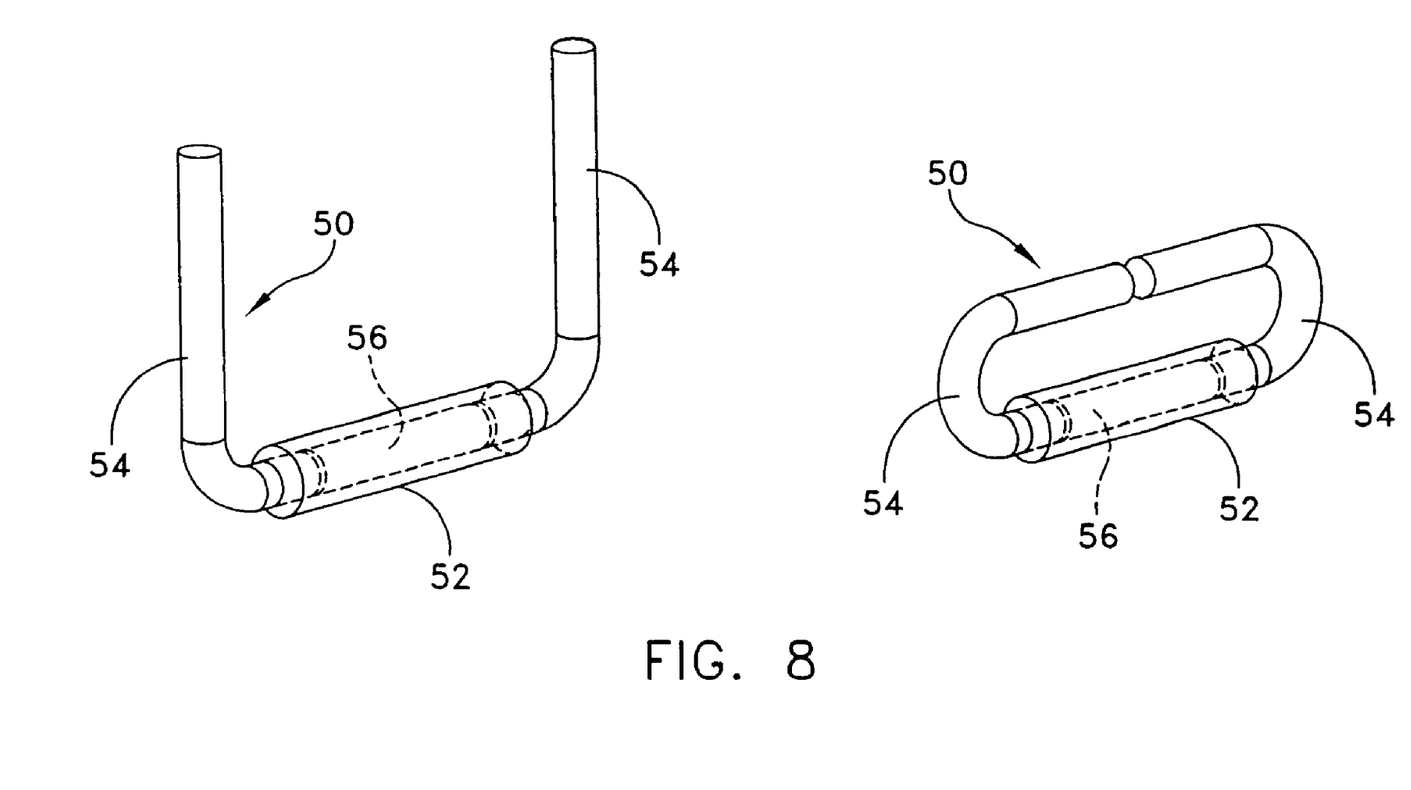
FIG. 8 illustrates still another staple configuration in accordance with the present invention.
Figure 9:
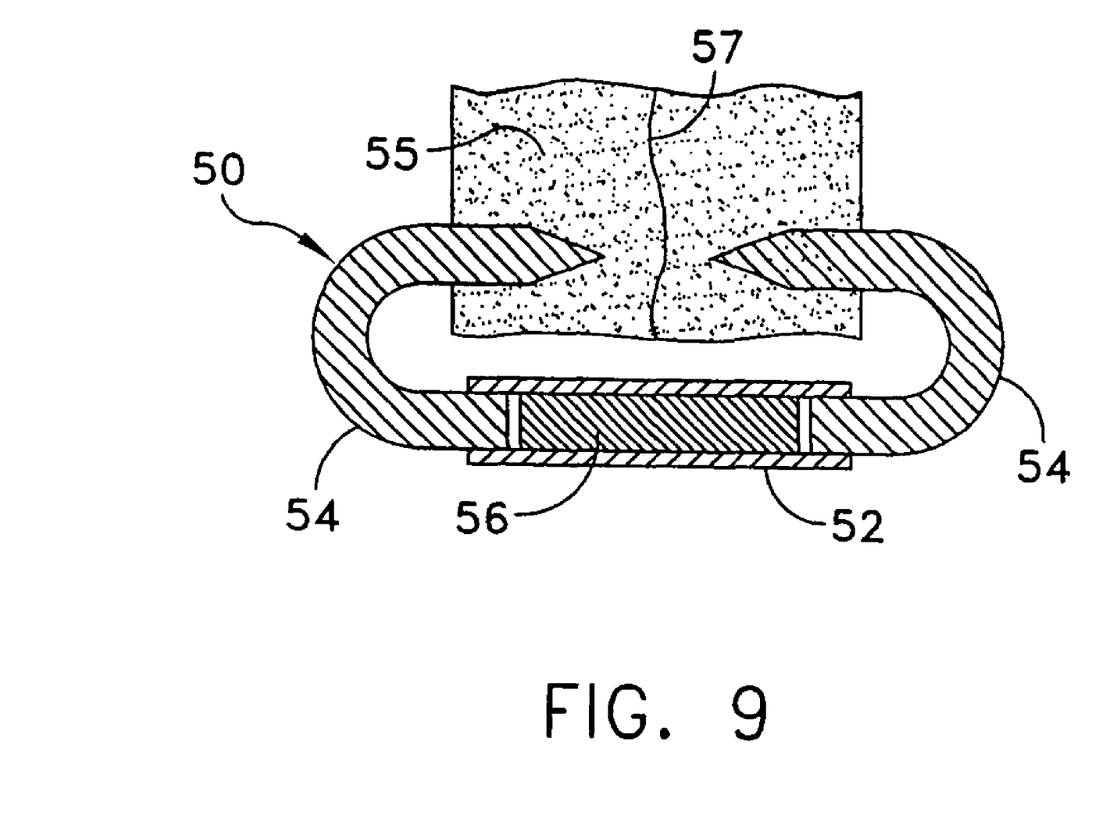
FIG. 9 is a cross-sectional view of the staple of FIG. 8 showing the staple closed to join tissue.

Reference is now made to FIG. 8 for an illustration of still another embodiment that incorporates the radioactive material inside the staple itself by sealing it within a cavity created, from a titanium tube. In FIG. 8 the staple is shown in both open and closed positions. Refer also to FIG. 9 for further details of this staple structure. FIG. 9 also illustrates the staple 50 as engaging a tissue 55 at incision 57. This staple 50 includes a cylindrical tube 52 that is preferably a titanium rube, but may also be of other metal materials. These materials include platinum, titanium, nickel-titanium alloys, gold, stainless steel, palladium, silica and alumina. The tube 52 defines a tubular cavity that is capped/sealed by titanium wires 54 that are laser-welded to the tube. The wires 54 serve as the legs of the staple.

In the embodiment shown in FIGS. 8 and 9 the radioactive material 56 is located inside the titanium tube which may be of ~0.40 mm in diameter with a wall thickness of ~0.07 mm, resulting in a cavity of 0.26 mm diameter. The ends of the tube 52 are plugged with titanium wires 54 of 0.25 mm diameter which may be laser-welded to the tubing. These wires 54 are typical of the wire-size currently used in surgical staples.

Such a tubular capsule of 0.40 mm diameter readily fits within the cavity of currently-used staple delivery systems.

One concern with the initial design concept of the source/staple is the degree to which the addition of asymmetric structure around the $^{169}$Ytterbium source modulates the dose distribution. We have made a preliminary assessment of this using the Monte Carlo technique. The Monte Carlo calculation was performed using the MCNP Version 5 Monte Carlo computer code, developed by LANL (MCNP5). The MCNP5 Monte Carlo code is a general neutron, photon, and electron radiation transport code that facilitates modeling complicated three-dimensional, heterogeneous geometrical structures such as medical sources and applicators. Its photon transport model includes photoelectric effect and accompanying fluorescence emission, coherent (Thomson) scattering, Compton scattering and pair production. A continuous-slowing-down model is used for electron transport that includes positrons, K x-rays and bremsstrahlung. MCNP is the only widely-used radiation transport code that permits coupled transport of photons, electrons, and neutrons.

Figure 10:
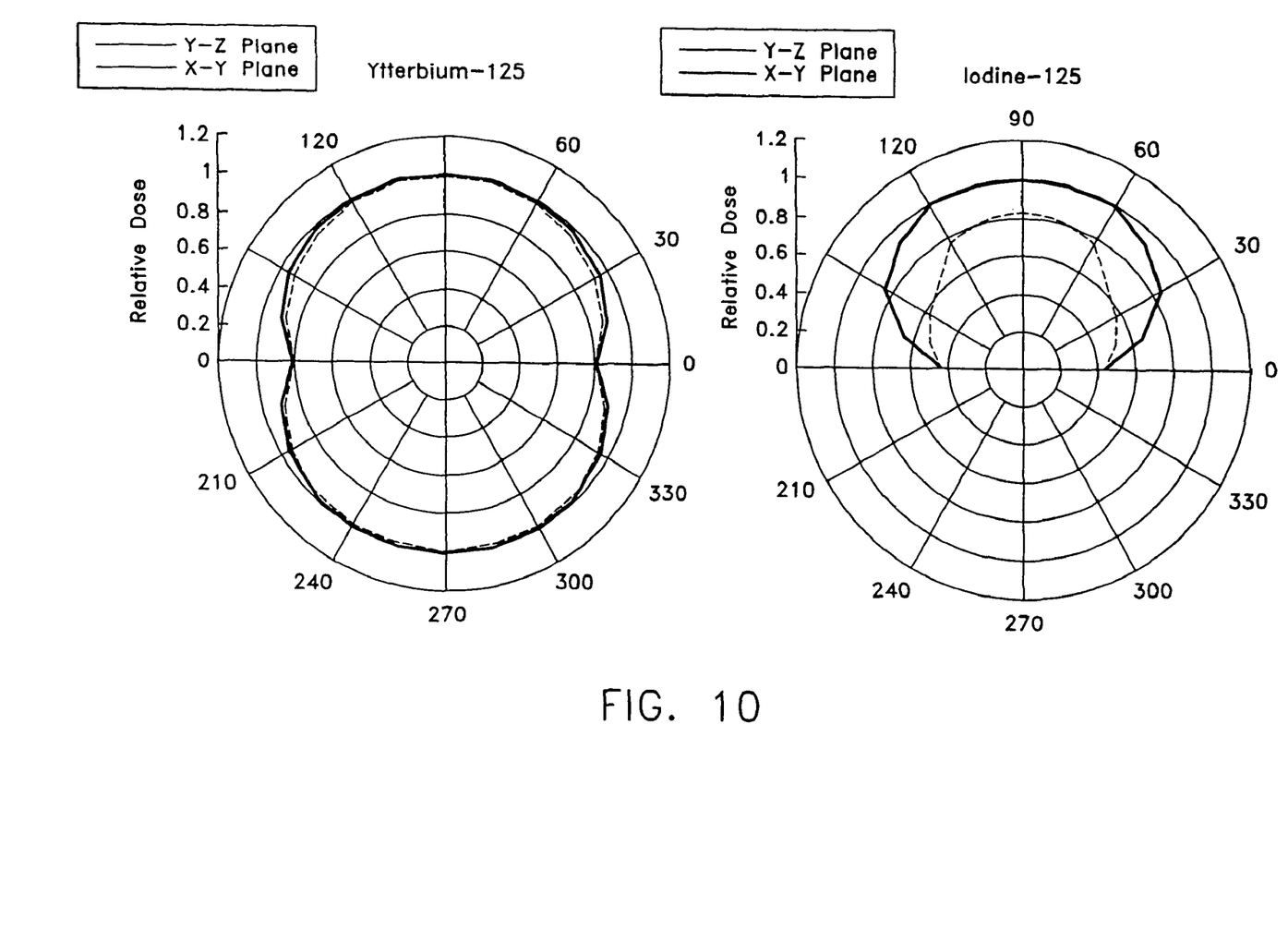
FIG. 10 illustrates dose distribution for the embodiment of FIG. 8.

The simulation geometry mimicked the geometrical and elemental compositions of the source/staple and its surroundings. The dose distribution in water was calculated for a radial distance of one centimeter in a plane containing the legs of the staple (Y-Z plane) and also in a plane perpendicular to the plane containing the legs of the staple (X-Z plane). Dosimetry data were calculated in each of these planes over angles ranging from 0° to 360° (in ten degree increments) using the *F8 tally in a 40 cm diameter phantom. Refer to FIG. 10 for two different sources as to their dose distribution at one centimeter from the source/staple in the plane containing the legs of the staple (Y-Z plane) and the plane perpendicular (X-Z plane). $^{169}$Ytterbium is shown on the left and $^{125}$Iodine is shown on the right.

The dose perturbation by the staple legs in the deployed (bent over) position for $^{169}$Ytterbium is very small (~4-5%) and is most predominant at oblique angles in the Y-Z plane (30°-45° and 135°-150°). This is much less than the perturbation observed for $^{125}$Iodine in these directions (~32%). The most significant perturbation occurs along the axis of the source/staple, which is common for all brachytherapy sources. In this case, the perturbation for $^{169}$Ytterbium (19%) is much less than that observed for $^{125}$Iodine (57%). This preliminary dose study shows that the anisotropy resulting from the $^{169}$Ytterbium source/staple is significantly better that that resulting from the $^{125}$Iodine source/staple.

Figure 11:
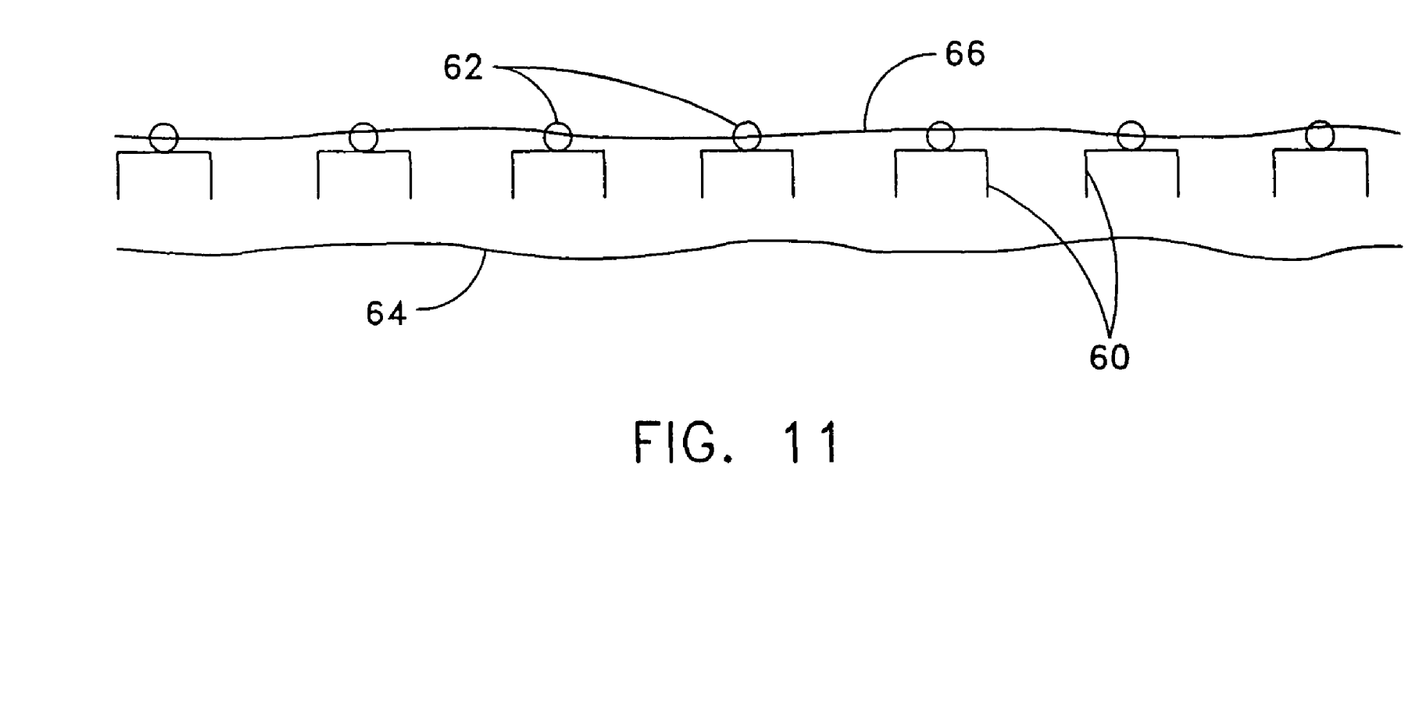
FIG. 11 schematically illustrates another embodiment of the present invention.

FIG. 11 shows still another embodiment for practicing the present invention. Instead of providing the radioactive source within the fastener or staple, in this embodiment there is schematically illustrated a series of staples 60 that may each be of conventional design but that have associated therewith a radioactive source shown at 62. The staples 60 are shown as associated with a surgical margin or incision 64. The sources 62 are distributed or positioned by means of a tie line 66. In an alternate arrangement a loop may be used at 62 and the line 66 may be a radioactive line supported by the loops 62 or the line 66 may carry spaced radioactive sources.

One of the main features of the present invention is the ability to apply a radioactive source concurrently with the fixing of the staple at the surgical margin or incision. This enables the source to be properly positioned for therapeutic purposes at the same time that the staple is used in its traditional sense as a joining means for tissue. For example, the concepts of the present invention can be used quite effectively in the treatment of lung cancer by the known surgical resection procedure. In the past radioactive sources were positioned after the basic operation was concluded, while in accordance with the present invention both the surgical step, as well as the source application step are provided at the same time and with only a single procedure step.

Having now described a limited number of embodiment of the present invention, it should be apparent to those skilled in the art that numerous embodiments and modifications thereof are contemplated as falling within the scope of the present invention as defined by the appended claims.

What is claimed is:

1. A device used for brachytherapy delivery in the treatment of cancer by radiation therapy, said device comprising:
a plurality of fastening means each in the form of a staple having a base and tissue piercing ends formed as respective legs of the staple;
said plurality of staples providing a staple array constructed and arranged to extend spaced apart, and extend substantially longitudinally of and substantially in parallel with a surgical margin;
a series of radioactive sources each in the form of a radioactive seed;
means for distributing the series of radioactive seeds in a linear array that extends substantially longitudinally of and substantially in parallel with the array of staples;
said array of radioactive seeds disposed adjacent to said array of staples, but remote from said surgical margin.

2. The device of claim 1 wherein said device is for a brachytherapy delivery system for applying a radioactive source to a tissue site at a resection margin.

3. The device of claim 1 including a sleeve for holding each said radioactive seed.

4. The device of claim 3 wherein said sleeve is constructed of any one of platinum, titanium, nickel-titanium alloys, gold, stainless steel, palladium, silica and alumina.

5. The device of claim 1 wherein the series of radioactive sources comprise a linear radioactive line.

6. The device of claim 1 wherein the means for distributing the series of radioactive seeds in a linear array comprises a tie line.

7. The device of claim 6 including respective loops for supporting the tie line.

8. A method for positioning a series of radioactive sources adjacent a surgical margin for therapeutic purposes, comprising the steps of;
providing a plurality of fastening means each in the form of a staple having a base and tissue piercing ends formed as respective legs of the staple;
said plurality of staples providing a linear staple array;
said staple array being adapted for use in a surgical procedure to join tissue at the surgical margin;
constructing and arranging said staple array so as to;
extend spaced apart,
extend substantially longitudinally of the surgical margin, and
extend substantially in parallel with the surgical margin,
providing a series of radioactive sources;
distributing the series of radioactive sources in a linear array so as to;
extend substantially longitudinally of the array of staples, and
extend substantially in parallel with the array of staples,
distributing the array of radioactive sources so that they are disposed adjacent to said array of staples, but remote from said surgical margin.

9. The method of claim 8 including applying the staples in sequence adjacent the surgical margin while substantially concurrently securing said radioactive sources in a fixed position adjacent said staples.

10. The method of claim 8 including applying the staples during a lung cancer resection procedure.

11. The method of claim 8 wherein the series of radioactive sources comprise a linear radioactive line.

12. The method of claim 1 wherein the step of distributing the series of radioactive seeds in a linear array includes providing a tie line.

13. The method of claim 12 including providing respective loops for supporting the tie line.

* * * * *